(12) United States Patent
Scheuing et al.

(10) Patent No.: US 9,636,057 B2
(45) Date of Patent: May 2, 2017

(54) CONFORMABLE PHYSIOLOGICAL SENSOR

(75) Inventors: Rick Scheuing, Rochester Hills, MI (US); Arik Anderson, Birmingham, MI (US); Oleg Gonopolskiy, West Bloomfield, MI (US)

(73) Assignee: Covidien LP, Mansfield, MA (US)

( * ) Notice: Subject to any disclaimer, the term of this patent is extended or adjusted under 35 U.S.C. 154(b) by 2042 days.

(21) Appl. No.: 12/268,245

(22) Filed: Nov. 10, 2008

(65) Prior Publication Data
US 2009/0131770 A1 May 21, 2009

Related U.S. Application Data

(60) Provisional application No. 60/986,726, filed on Nov. 9, 2007.

(51) Int. Cl.
*A61B 5/1455* (2006.01)
*A61B 5/145* (2006.01)
*A61B 5/00* (2006.01)

(52) U.S. Cl.
CPC ...... *A61B 5/14552* (2013.01); *A61B 5/14546* (2013.01); *A61B 5/6833* (2013.01); *A61B 2562/0233* (2013.01); *A61B 2562/043* (2013.01); *A61B 2562/164* (2013.01)

(58) Field of Classification Search
CPC ............ A61B 5/14551; A61B 5/14552; A61B 5/14553; A61B 5/6832; A61B 5/6833; A61B 2562/164; A61B 2562/166
USPC ........ 600/309, 310, 322, 323, 344; 606/2, 9, 606/13
See application file for complete search history.

(56) References Cited

U.S. PATENT DOCUMENTS

| | | | |
|---|---|---|---|
| 5,584,296 A * | 12/1996 | Cui et al. ....................... | 600/479 |
| 5,879,373 A * | 3/1999 | Roper et al. .................. | 600/344 |
| 7,190,986 B1 * | 3/2007 | Hannula et al. ............... | 600/344 |
| 7,706,853 B2 * | 4/2010 | Hacker et al. ................. | 600/344 |
| RE41,317 E * | 5/2010 | Parker ........................... | 600/344 |
| RE43,860 E * | 12/2012 | Parker ........................... | 600/344 |
| 8,428,682 B1 * | 4/2013 | Rood .................. | A61B 5/0408 600/391 |
| 2002/0165440 A1 * | 11/2002 | Mason et al. ................. | 600/344 |
| 2007/0123756 A1 * | 5/2007 | Kitajima et al. .............. | 600/300 |
| 2008/0076996 A1 * | 3/2008 | Hoarau ......................... | 600/344 |
| 2008/0242958 A1 * | 10/2008 | Al-Ali et al. ................. | 600/323 |

FOREIGN PATENT DOCUMENTS

| | | |
|---|---|---|
| WO | WO-9427494 A | 12/1994 |
| WO | WO-0059374 A | 10/2000 |

OTHER PUBLICATIONS

PCT International Search Report for PCT/US2008/083055 dated Mar. 11, 2009.

* cited by examiner

*Primary Examiner* — Adam J Eiseman
(74) *Attorney, Agent, or Firm* — Harness, Dickey & Pierce PLC

(57) ABSTRACT

A sensor for measuring physiological characteristics includes a circuit assembly, at least one material layer, and an adhesive layer that extends beyond an outer edge of the circuit assembly. The at least one material layer forms an adhesive edge around the perimeter of the sensor.

19 Claims, 6 Drawing Sheets

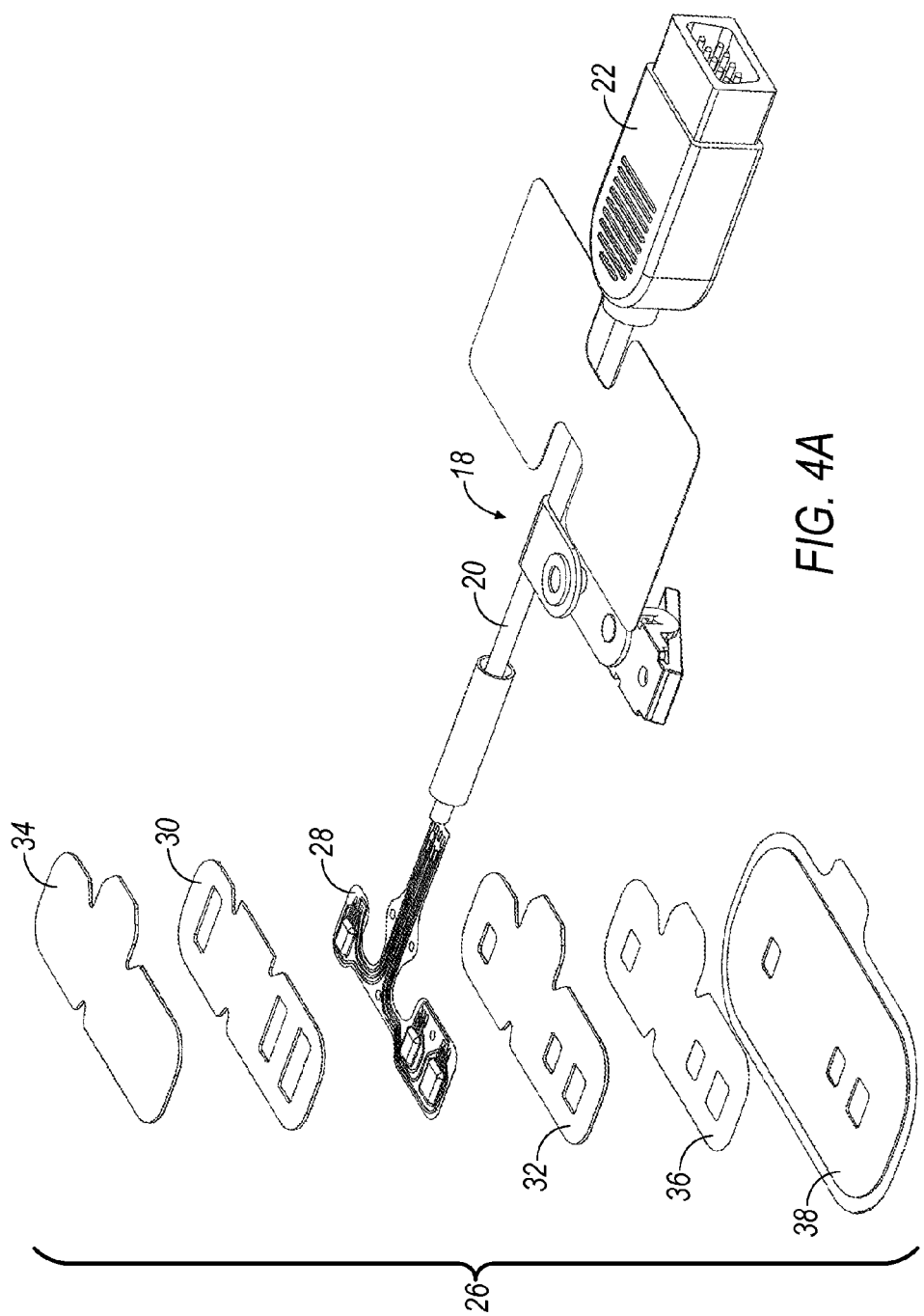

CONFORMABLE PHYSIOLOGICAL SENSOR

CROSS REFERENCE TO RELATED APPLICATIONS

This application claims priority to U.S. Ser. No. 60/986,726 filed on Nov. 9, 2007, which is hereby incorporated by reference in its entirety.

BACKGROUND

Physiological sensor systems are used to measure a variety of physiological characteristics such as blood metabolite and oxygen saturation in body tissues using multiple wavelengths of light. Physiological sensor systems generally include a monitoring system connected to a sensor pad that adheres to the portion of the body being tested. The sensor pad includes a plurality of optical components that generally protrude through the outer surface of the sensor pad. The thickness and configuration of the optical components on the pad often generate pressure points when external force or pressure is applied. These pressure points can be painful and damaging to sensitive skin, particularly in neonates when the sensor pad is secured to the body by a head band, cap or other means.

In addition, known sensor systems, although flexible, have a certain degree of stiffness that often causes the sensor to lift or peel from the patient and limits the adhesion of the sensor to small radius compound curvatures that are often encountered in neonatal patients.

Accordingly, the embodiments described hereinafter were developed in light of these and other drawbacks associated with existing physiological sensor pads.

BRIEF DESCRIPTION OF THE DRAWINGS

FIG. 4A illustrates an exploded view of an exemplary t-shape physiological sensor;

DETAILED DESCRIPTION

A physiological sensor that adheres and conforms to small radius compound curvatures is provided. The sensor is a non-invasive, disposable sensor with a multi-layered structure that includes a sensor pad assembly having a flexcircuit assembly disposed between atleast a top layer and a bottom layer. The flexcircuit assembly includes a plurality of optical components disposed along a mechanical neutral axis of the flexcircuit assembly. To maximize flexibility, the optical components are considerably thicker than the flexcircuit, protruding above and below the flexcircuit when viewed from the side. The sensor pad assembly also includes a patient adhesive layer on the bottom, patient side surface of the sensor that is used to secure the sensor assembly to the patient. In one embodiment, the flexcircuit and padding assemblies are substantially the same size and shape as the patient adhesive layer. In another embodiment, the sensor pad assembly layers are smaller in size and shape than the patient adhesive layer such that the patient adhesive layer extends beyond the edges of the sensor pad assembly layers.

Figure 1:
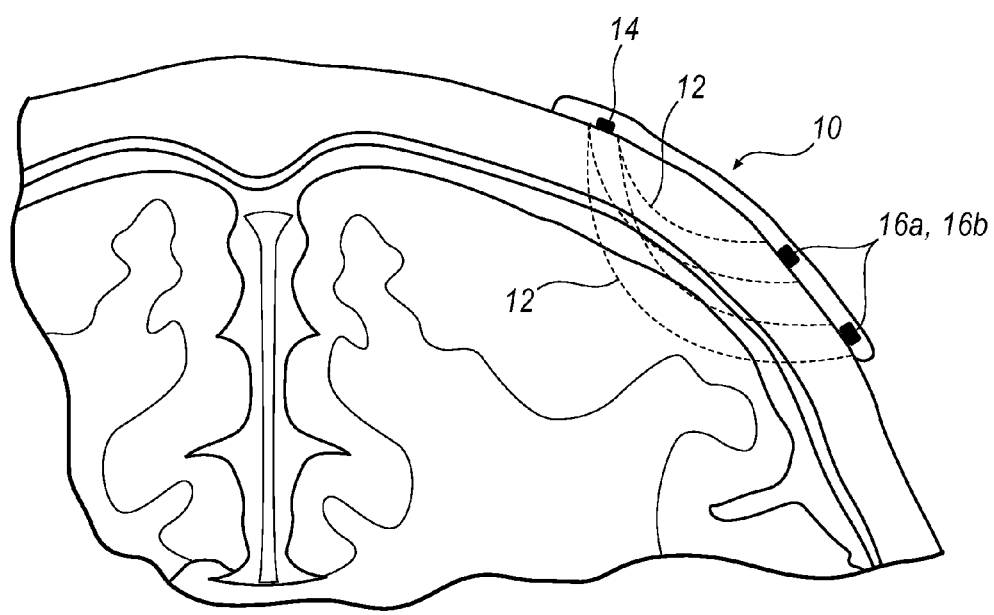
FIG. 1 illustrates a method of operation for an exemplary physiological sensor.

FIG. 1 illustrates an exemplary physiological sensor 10 as applied to a patient for measuring a physiological characteristic such as blood metabolite. The sensor 10 operates by emitting light of a plurality of near infrared wavelengths 12 and measuring its transmitted and reflected intensities at a plurality of unequal distances from the emitter locations. This information is used to calculate blood metabolite and other physiological measurements. The sensor 10 of FIG. 1 is exemplary in that it includes one light source 14 and two detectors, one configured for shallow detection 16a and one configured for deep detection 16b. However, alternative embodiments may include a plurality of light sources 14 with any number of detectors 16a, 16b in any configuration. In addition, although there is a single light source shown, each light source may be capable of emitting multiple wavelengths of light.

Figure 2:
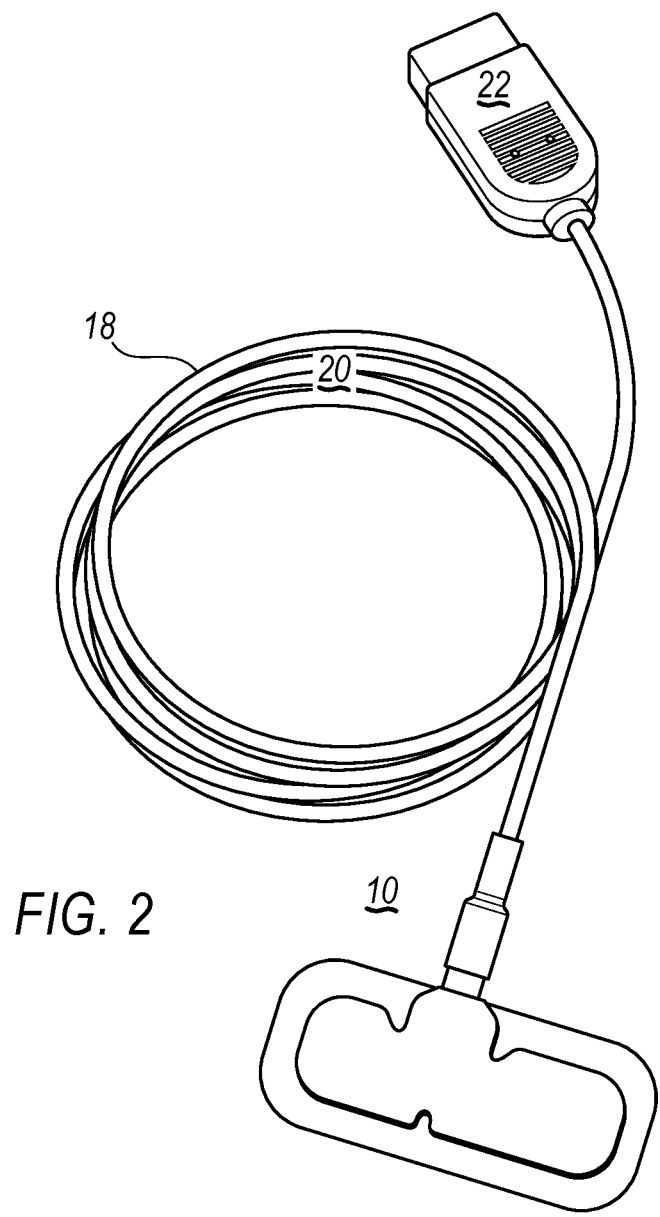
FIG. 2 illustrates a top view of an exemplary t-shape physiological sensor and cable assembly.
Figure 3:
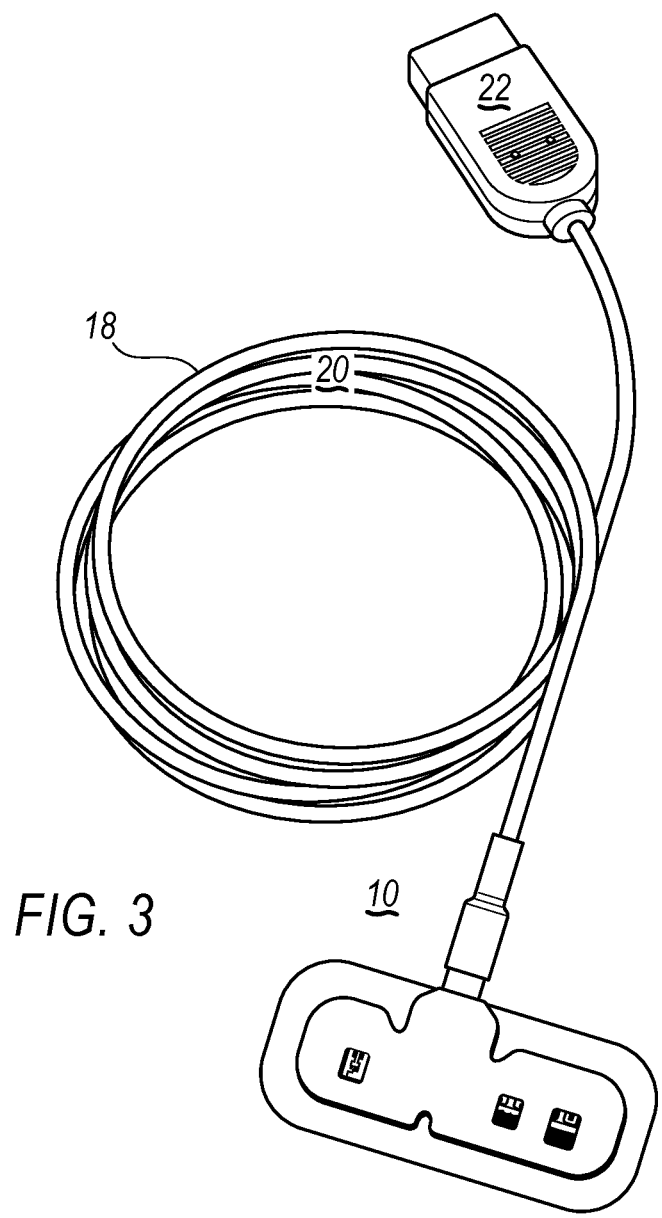
FIG. 3 illustrates a patient side view of an exemplary t-shape physiological sensor and cable assembly.

FIGS. 2 and 3 illustrate a top view and patient side view, respectively, of an exemplary t-shape physiological sensor 10 attached to a cable assembly 18. The cable assembly 18 generally includes a cable 20 that extends from a portion of sensor 10 to a connector 22, which is generally a quick disconnect configured to plug into a monitoring system that operates with the sensor to measure one or more physiological characteristics.

FIG. 4A illustrates an exploded view of an exemplary t-shape sensor 24 attached to a cable assembly 18 having a cable 20 and a connector 22. The t-shape sensor 24 has a multi-layered sensor pad assembly 26 with a flexcircuit 28 disposed between a plurality of material layers. The material layers vary in shape, size and thickness and can be in the form of adhesive, tape, foam, or any other suitable material. One non-limiting example is a Polyethylene foam medical tape such as a 3M 1774T. In one exemplary approach, the flexcircuit is disposed between a mid layer tape 30 and a bottom layer tape 32. The sensor pad assembly 26 further includes a top layer tape 34, an optional bottom layer adhesive 36 and a patient side adhesive 38.

Figure 4B:
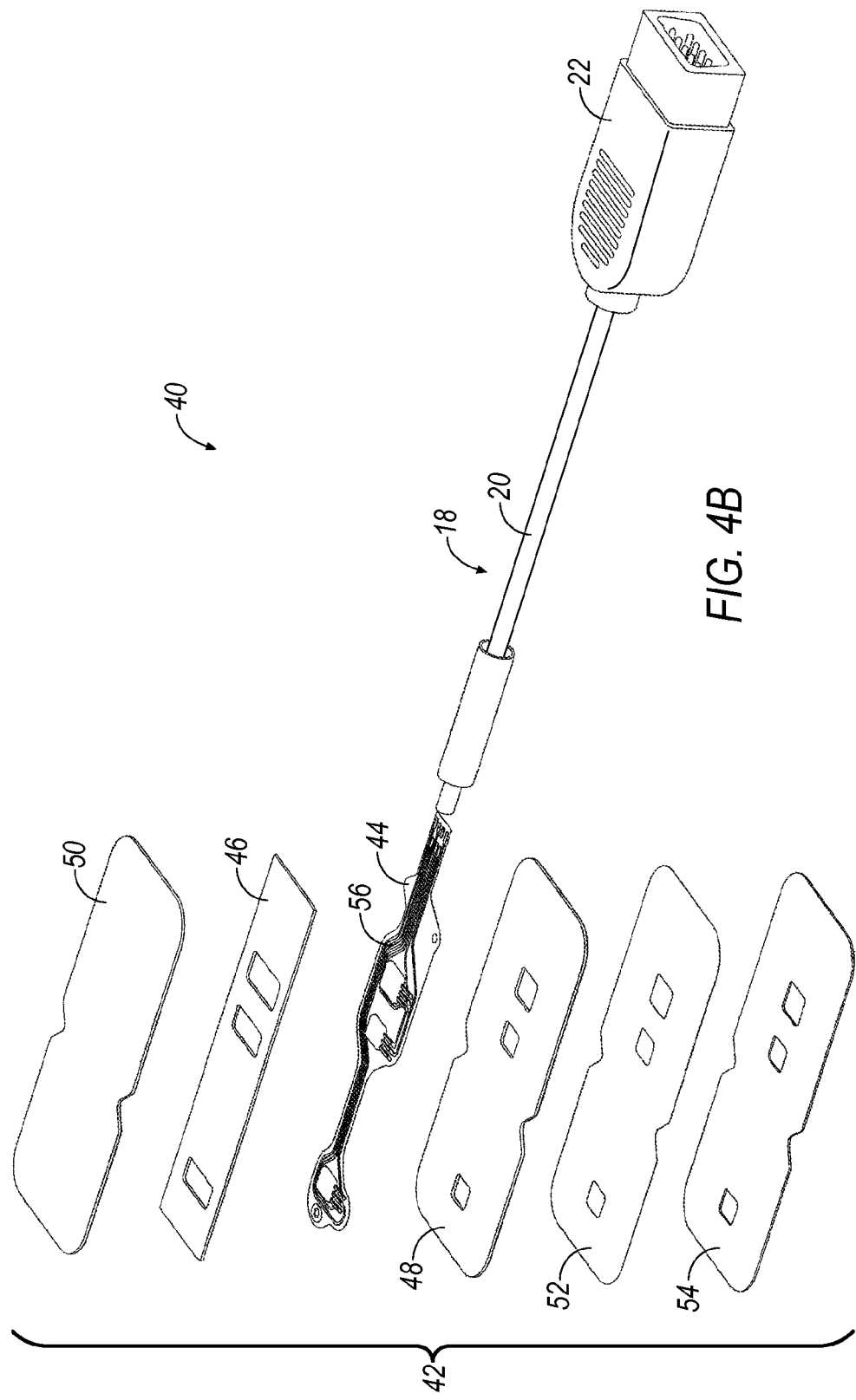
FIG. 4B illustrates an exploded view of an exemplary in-line physiological sensor.

Similarly, FIG. 4B illustrates an exploded view of an exemplary in-line sensor 40 attached to a cable assembly 18 having a cable 20 and a connector 22. Like the t-shaped sensor 24 of FIG. 4A, the in-line sensor 40 has a multi-layered sensor pad assembly 42 with a flexcircuit 44 disposed between a mid layer tape 46 and a bottom layer tape 48. The sensor pad assembly 42 further includes a top layer tape 50, an optional bottom layer adhesive 52 and a patient side adhesive 54. The patient side adhesive 54 may be opaque or generally translucent. In one embodiment, the patient adhesive layer includes a hydrocolloid adhesive, which is recommended by the National Association of Neonatal Nurses for skin application because it is less aggressive than the medical grade acrylic adhesive that is typically used on known physiological sensors. Hydrocolloid adhesive is generally used for wound care or as a buffer for other devices with more aggressive adhesives. The hydrocolloid adhesive allows the sensor pad to be easily applied to and removed from delicate patient skin. Alternatively, patient side adhesive 54 can be a silicone based adhesive such as MED 5585H.

Being either t-shaped or in-line generally refers to the orientation of the cable 20 with respect to the flexcircuit 28, 44. For example, the t-shape sensor 24 is configured such that the cable intersects perpendicularly with the flexcircuit 28, while with the in-line sensor 26, the cable extends linearly with flexcircuit 44.

In one exemplary approach, the patient adhesive layer 38, 54 is substantially the same size and shape as the bottom layer tape 32, 48. However, in another exemplary approach, as shown in at least FIGS. 2-3 and 4A, the perimeter dimensions of the top layer tape 34, 50, mid layer tape 30, 46 and bottom layer tape 36, 52 are smaller than that of the patient side adhesive 38, 54 creating an adhesive edge around the perimeter of the sensor pad assembly. Because the patient side adhesive 38, 54 is generally soft, stretchy and flexible, the outer edges of the sensor pad assembly are highly conformable to the small radius compound curvatures that are often encountered in neonatal patients. In this way, the edges of the sensor are less likely to lift and peel away from the patient's skin.

In some embodiments, the sensor pad assembly includes a deformable layer configured to conform to and maintain a compound curvature shape once the sensor is applied to the patient. This layer could also be used to reflect and intensify the emitted light. The deformable layer may be aluminum or any other material suitable for conforming to and maintaining its shape. In lieu of, or in addition to the deforming layer, the conforming capacity of the sensor could also be accomplished by varying the shape, thickness and metallization of the flexcircuit tracing 56. In other words, the sensor's ability to conform and maintain its shape can be in whole, or in part, due to the characteristics of the flexcircuit.

Figure 5:
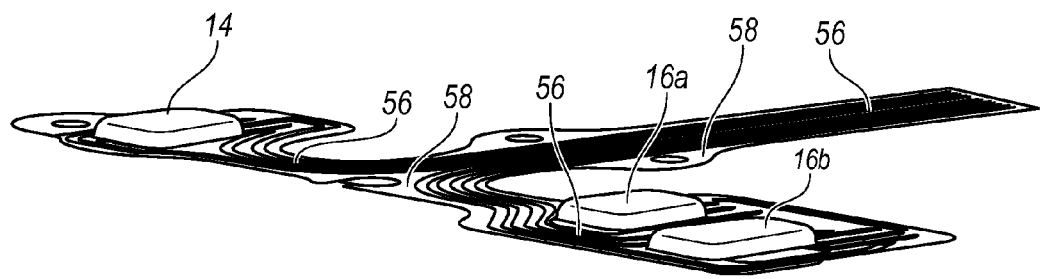
FIG. 5 illustrates a side view of an exemplary flexcircuit assembly for a t-shape physiological sensor.
Figure 6:
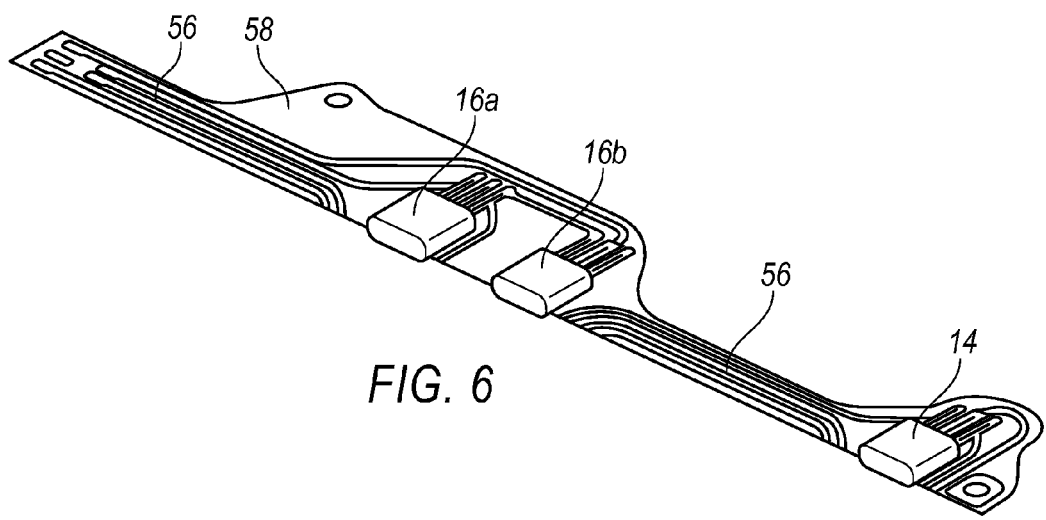
FIG. 6 illustrates a side view of an exemplary flexcircuit assembly for an in-line physiological sensor.

FIGS. 5 and 6 illustrate top perspective views of exemplary the flexcircuit assemblies 28, 44 for a t-shape sensor 24 and an in-line sensor 26, respectively. Each flexcircuit assembly includes a plurality of optical components 16a, 16b mounted to the flexcircuit 58 such that the horizontal plane of the flexcircuit is axially aligned with the mechanical center of each of the optical components. In this way, the pad layer materials (i.e., the top and bottom layer tapes) when assembled on both the patient side and the opposite side of the flexcircuit 58 equal the thickness of the optical components 16a, 16b, which minimizes potential pressure points generally caused by the optical component thickness. The assembled sensor is configured to conform to a shape approximating the smallest compound curvature of a human head. The assembled sensor adheres to the patient surface indefinitely with no external force or pressure, minimizes potential pressure points, is easily applied to and removed from delicate patient skin and can be calibrated accurately and repeatably. The sensor has the capability of conforming to the relatively small radius compound curvature of neonates for cerebral and somatic applications and can also be used to enhance pediatric and adult applications. The sensor pad assembly has uniform patient side and top side surfaces that minimize potential pressure points. In other words, the sensor pad assembly 26, 42 has an overall uniform thickness with no protrusions on either side of the sensor pad.

In one embodiment, the flexcircuit 58, optical components 16a, 16b and cable assembly 18 are procured as a subassembly and the optics and cable are electrically connected to the flexcircuit 58. Once the subassembly is tested and calibrated, the pad layers and the patient side adhesive are laminated on each side of the flexcircuit 58 to form the pad assembly 26, 42 according to the exploded view in FIGS. 4A and 4B. In one embodiment, the pad layer lamination is achieved using specific adhesives that are procured already laminated to each layer. The pad layers are made using laminating machines and die cutting or laser cutting tools.

In one embodiment, copper traces 56 are used to provide electrical connectivity between flexcircuit components. In contrast to silver ink traces, which are generally used in some known sensor configurations, copper traces have a relatively high conductivity and can be narrower than silver ink. This allows the flexcircuit to be considerably narrower to maximize its ability to conform to compound curvature.

It is to be understood that the above description is intended to be illustrative and not restrictive. Many alternative approaches or applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. In sum, it should be understood that the invention is capable of modification and variation and is limited only by the following claims.

The present embodiments have been particularly shown and described, which are merely illustrative of the best modes. It should be understood by those skilled in the art that various alternatives to the embodiments described herein may be employed in practicing the claims without departing from the spirit and scope as defined in the following claims. It is intended that the following claims define the scope of the invention and that the method and apparatus within the scope of these claims and their equivalents be covered thereby. This description should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

All terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary.

What is claimed is:

1. A sensor for measuring physiological characteristics, comprising:

a circuit assembly mounted on a flexible planar substrate that includes a plurality of optical components, said flexible planar substrate having a patient surface configured to be directed toward a patient and a top surface configured to be directed away from the patient when the sensor is affixed to the patient;

at least one material layer proximate to said flexible planar substrate; and an adhesive layer on the patient side of said flexible planar substrate and configured to adhere the sensor to a surface of the patient;

wherein an entire perimeter of said adhesive layer extends beyond a perimeter of said flexible planar substrate and a perimeter of said material layer of the sensor having the largest perimeter, such that the perimeter of the adhesive layer defines the overall shape and size of the sensor, wherein said optical components are mounted in and pass through orifices that extend through said flexible planar substrate and a center longitudinal axis of each said optical component is aligned with and coincides with a center horizontal plane of said flexible planar substrate.

2. The sensor of claim 1, wherein a center horizontal plane of said flexible planar surface is axially aligned with the mechanical center of said optical components.

3. The sensor of claim 1, wherein said optical components are mounted such that half of each component mounted in said orifice extends above a center horizontal plane of said flexible planar substrate and the other half of each component mounted in said orifices extends below said center horizontal plane of said flexible planar substrate.

4. The sensor of claim 1, wherein a center of the optical components is axially aligned with the plane defined by the flexible planar substrate.

5. The sensor of claim 1, wherein said sensor includes at least two material layers, and said flexible planar substrate is disposed between said two material layers.

6. The sensor of claim 5, wherein a thickness of said two material layers equals a thickness of said optical component having the greatest thickness.

7. The sensor of claim 1, wherein said sensor is configured to conform to the shape of a surface of a patient, and to maintain the conformed shape independent of adhesion force applied by said adhesive layer.

8. The sensor of claim 1, further comprising a deformable layer disposed within said sensor and configured to conform to the shape of a surface of a patient, and to maintain the conformed shape independent of adhesion force applied by said adhesive layer.

9. The sensor of claim 8, wherein said deformable layer is a metal layer.

10. The sensor of claim 1, wherein said optical components include a light source and a light detector.

11. A sensor, comprising:
a circuit assembly mounted on a flexible planar substrate that includes a plurality of optical components, said flexible planar substrate having a patient surface configured to be directed toward a patient and a top surface configured to be directed away from the patient when the sensor is affixed to the patient;
at least two material layers, wherein said flexible planar substrate is disposed between said two material layers; and
wherein said optical components are mounted in and pass through orifices that extend through said flexible planar substrate;
wherein a center of the optical components is axially aligned with the plane defined by the flexible planar substrate.

12. The sensor of claim 11, further comprising an adhesive layer on the patient side of said flexible planar substrate, wherein an entire perimeter of said adhesive layer extends beyond a perimeter of said flexible planar substrate and a perimeter of said material layer of the sensor having the largest perimeter, such that the perimeter of the adhesive layer defines the overall shape and size of the sensor.

13. The sensor of claim 11, wherein a center longitudinal axis of each said optical component is aligned with and coincides with a center horizontal plane of said flexible planar substrate.

14. The sensor of claim 11, wherein said optical components are mounted such that half of each component mounted in said orifice extends above a center horizontal plane of said flexible planar substrate and the other half of each component mounted in said orifices extends below said center horizontal plane of said flexible planar substrate.

15. The sensor of claim 11, wherein said sensor is configured to conform to the shape of a surface of a patient, and to maintain the conformed shape independent of adhesive force applied by said adhesive layer.

16. The sensor of claim 11, further comprising a metal layer disposed within said sensor and configured to conform to the shape of a surface of a patient and to maintain the conformed shape independent of adhesion force applied by said adhesive layer.

17. A sensor, comprising:
a circuit assembly mounted on a flexible planar substrate that includes at least a light source and a light detector, said flexible planar substrate having a patient surface configured to be directed toward a patient and a top surface configured to be directed away from the patient when the sensor is affixed to the patient;
at least two material layers, wherein said flexible planar substrate is disposed between said two material layers;
an adhesive layer on the patient side of said flexible planar substrate, wherein an entire perimeter of said adhesive layer extends beyond a perimeter of said flexible planar substrate and a perimeter of said material layers of the sensor having the largest perimeter, such that the perimeter of the adhesive layer defines the overall shape and size of the sensor; and
wherein said light source and light detector are mounted in orifices in said flexible planar substrate such that said light source and said light detector extend through said flexible planar substrate;
wherein a center longitudinal axis of each said light source and light detector is aligned with and coincides with a center horizontal plane of said flexible planar substrate.

18. The sensor of claim 17, wherein said light source and said light detector are mounted such that half of each said light source and light detector mounted in said orifice extends above a center horizontal plane of said flexible planar substrate and the other half of each said light source and light detector mounted in said orifices extends below said center horizontal plane of said flexible planar substrate.

19. The sensor of claim 17, wherein said sensor is configured to conform to the shape of a surface of a patient, and to maintain the conformed shape independent of adhesion force applied by said adhesive layer.

* * * * *